Figure 4A:
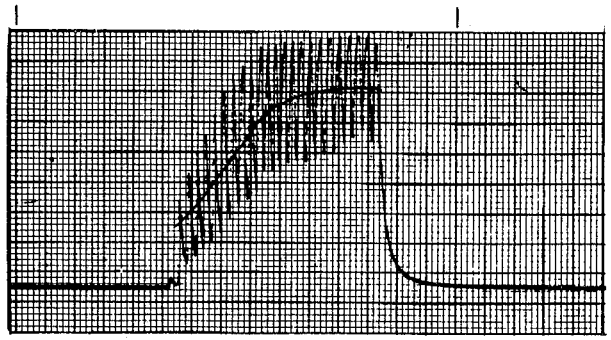
Figure 4A:
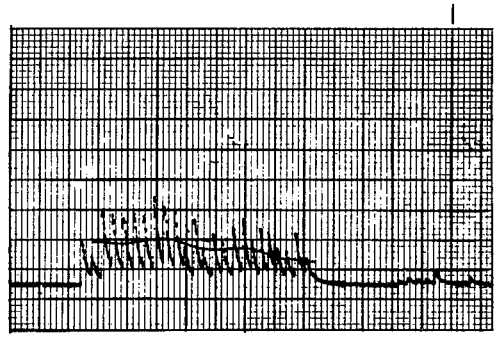

United States Patent [19]
Bell, Jr. et al.

[11] 3,971,034
[45] July 20, 1976

[54] PHYSIOLOGICAL RESPONSE ANALYSIS METHOD AND APPARATUS

[75] Inventors: Allan D. Bell, Jr., Annandale; Wilson H. Ford, Arlington; Charles R. McQuiston, Falls Church, all of Va.

[73] Assignee: Dektor Counterintelligence and Security, Inc., Springfield, Va.

[22] Filed: Sept. 5, 1972

[21] Appl. No.: 286,426

Related U.S. Application Data

[63] Continuation of Ser. No. 113,949, Feb. 9, 1971, abandoned.

[52] U.S. Cl. .................................. 346/1; 128/21 R; 179/1 SP; 324/77 A; 346/13; 346/33 R
[51] Int. Cl.² .......................................... G01D 1/04
[58] Field of Search ............. 346/33 R, 33 ME, 13; 179/1 VS, 1 SA; 128/2 R, 2.1 R; 324/77 A

[56] References Cited
UNITED STATES PATENTS

| | | | |
|---|---|---|---|
| 2,181,265 | 11/1939 | Dudley | 179/100.1 VS |
| 3,195,533 | 7/1965 | Fisher | 128/2.1 |
| 3,221,334 | 11/1965 | Jones | 346/33 |

Primary Examiner—Joseph W. Hartary
Attorney, Agent, or Firm—Roylance, Abrams, Berdo & Kaul

[57] ABSTRACT

A method of detecting psychological stress by evaluating manifestations of physiological change in the human voice wherein the utterances of a subject under examination are transduced to electrical signals and processed to emphasize selected characteristics which have been found to change with psycho-physiological state changes. The processed signals are then displayed, as on a strip chart recorder, for observation, comparison and analysis. An especially useful characteristic is an infrasonic modulation in the voice. Apparatus for performing detection of this type includes a transducer, a magnetic recorder, a series diode, a plurality of integrating capacitors, an amplifier and a chart recorder. A second apparatus includes filter means, an FM discriminator and a detector, a waveform integrator, an amplifier and a recorder for producing a visible record.

9 Claims, 10 Drawing Figures

FIG. 1
FIG. 2
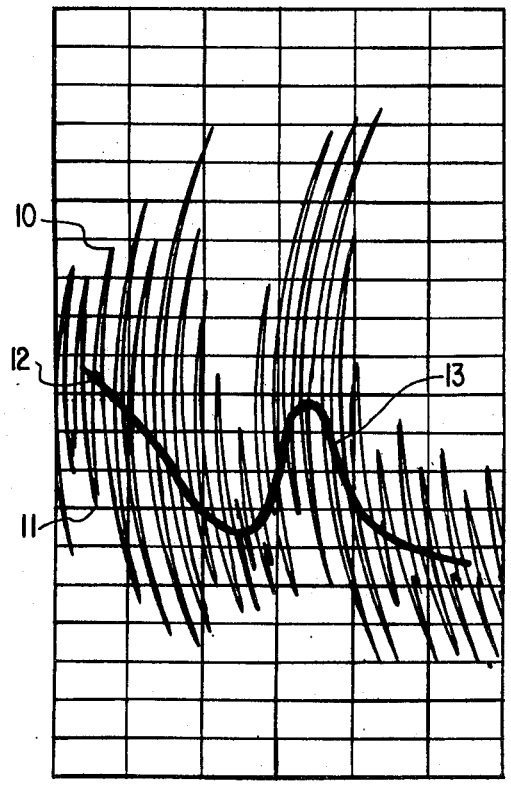
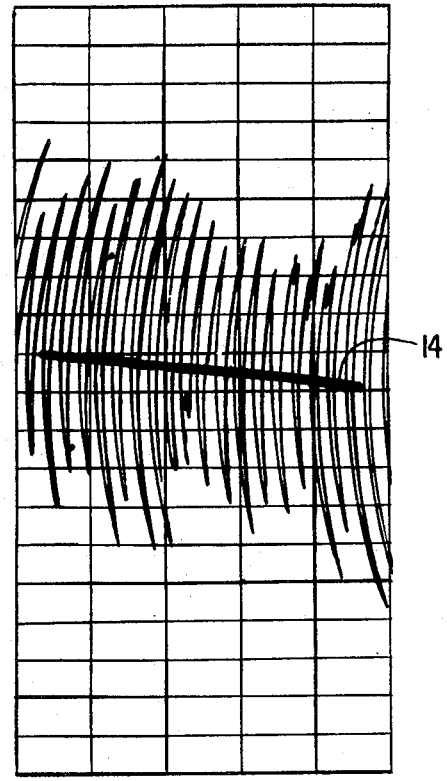
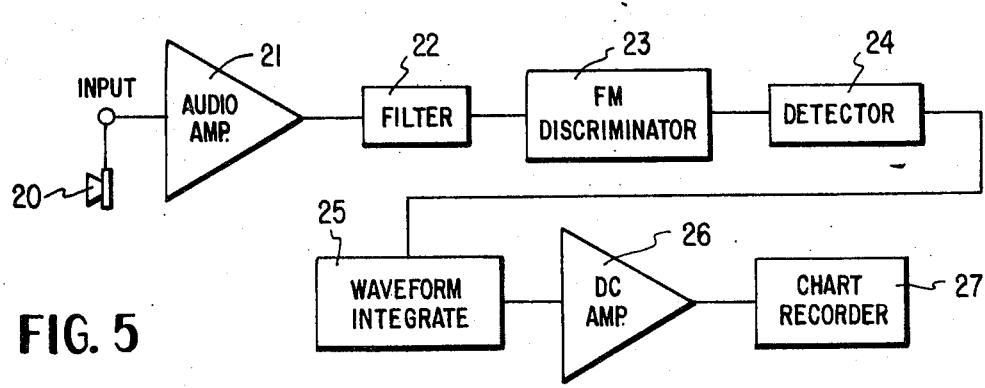
FIG. 5
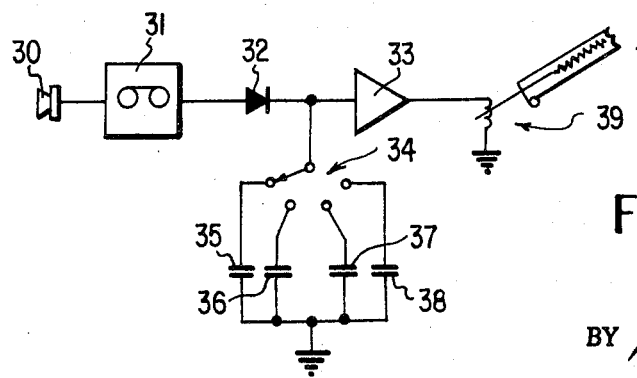
FIG. 6
INVENTORS.
ALLAN D. BELL, JR.
WILSON H. FORD
CHARLES R. McQUISTON
BY *Roylance, Abrams, Berdo & Kaul*
ATTORNEYS.

FIG. 3a
FIG. 3b
FIG. 3c
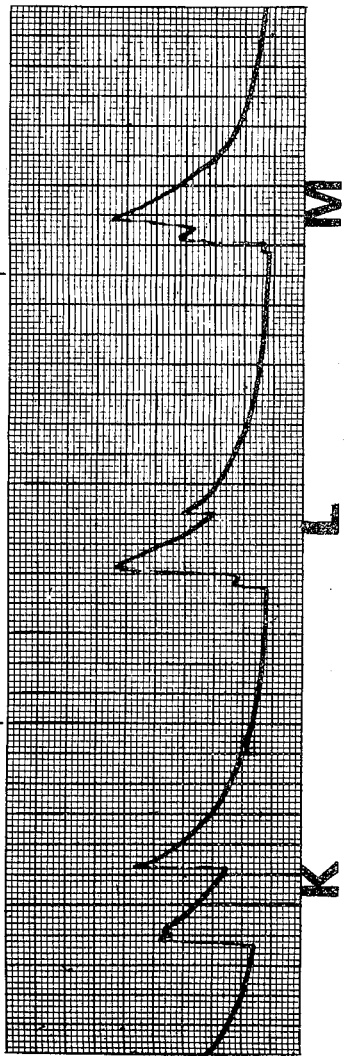
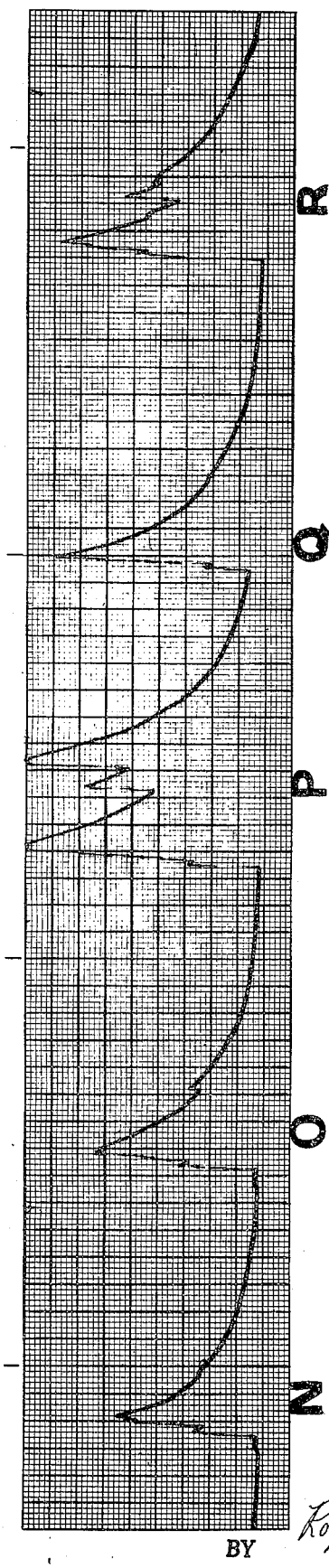
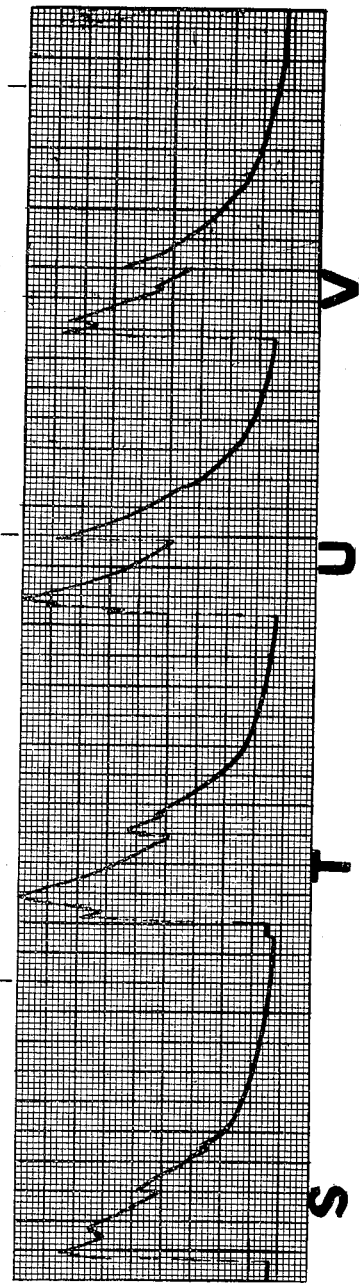
INVENTORS.
ALLAN D. BELL, JR.
WILSON H. FORD
CHARLES R. McQUISTON
BY *Roylance, Abrams, Berdo & Kaul*
ATTORNEYS.

PHYSIOLOGICAL RESPONSE ANALYSIS METHOD AND APPARATUS

This is a continuation of application Ser. No. 113,949, filed Feb. 9, 1971, now abandoned.

This invention relates to a method of detecting and measuring psychological stress and to an apparatus for accomplishing the method.

Throughout history, various societies have recognized the fact that there is a relationship between psychological stress and changes in physiological states. One manner in which this relationship has been employed is in the causation of programmed response to psychological stimuli, a technique which has most notably been documented by Pavlov in his experiments with conditioned responses. Essentially the same characteristics have provided some basis for the development of techniques in such diverse fields as applied psychology, advertising and hypnotism. Although the existence of this aspect of the psycho-physiological relationship is well recognized, it is only indirectly involved with the present invention.

The second general type or category of the psycho-physiological relationship, which is of more direct interest to the present invention, involves the recognition and identification of physiological changes which occur when the psychological changes take place. This approach is used more often in medical and psychological research and diagnosis, and in lie detection.

If the physiological manifestations of a change in psychological state are sufficiently great, it is possible for some subjective evaluations to be made by visual, unaided observation by a trained observer. However, far more accurate evaluation can be made by instrumentation designed to detect and measure relatively small degrees of physiological change. Those physiological changes most usually considered are brain wave patterns, heart activity, skin conductivity and breathing activity. One example of such a technique is found in U.S. Pat. No. 1,788,434 to Leonarde Keeler.

While the measurement of these activities does provide a far more accurate evaluation of physiological response than does direct unaided observation, it introduces several disadvantages. The most functionally serious of these problems is the artificiality of the testing situation caused largely by the previous requirement that sensors be attached to the person who is the subject of the examination. In addition, techniques heretofore used have generally required a controlled environment with resultant restrictions on the normal activity of the subject. These requirements can be expected to induce a psychological "set" in the subject which, in some cases, may be as strong as, or stronger than, the psychological set which is to be evaluated, thereby substantially reducing the validity of the evaluation.

An object of the present invention is to provide a method of evaluating psychological stress by detecting and measuring manifestations of physiological changes wherein the traditional restraints are minimized or eliminated to the extent that, in some cases, the subject under examination need not know that he is being examined.

A further object of the invention is to utilize the human voice as the medium by which changes in physiological state in response to psychological stress are detected.

A further object is to provide an apparatus for providing a visible record of those characteristics of the human voice by which physiological changes can be detected and from which the existence of psychological stress can be determined.

Briefly described, the method of the invention includes the steps of recording oral utterances of a subject on a visually observable medium and identifying frequency components of the recorded utterances which indicate physiological manifestations of the psychological stress. More specifically, the frequency components which can be identified as indicating the physiological state changes involve, in part, the infrasonic variations between utterances of a subject, changes in the infrasonic frequency variations being indicative of stress.

The apparatus of the invention includes transducer means for converting oral utterances of a subject into electrical signals, means for converting the frequency modulations in those electrical signals to amplitude modulations, and then recording the amplitude modulations thus produced on a visible record which can then be observed to detect indications of psychological stress.

Figure 4B:
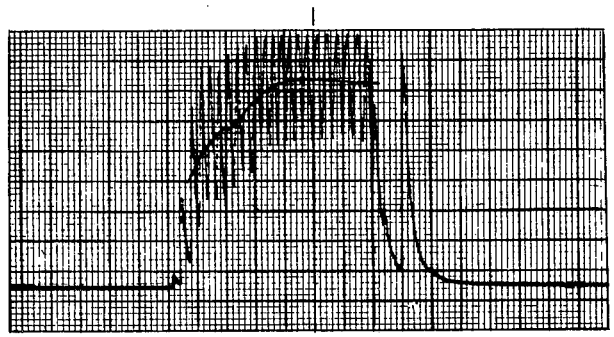
Figure 4B:
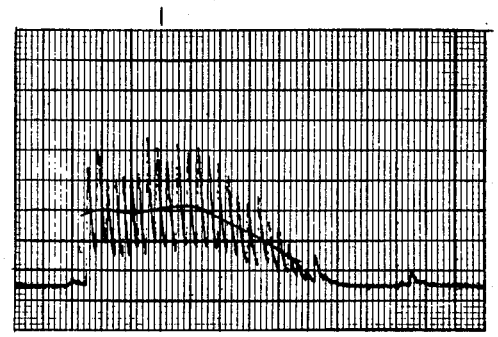
Figure 4C:
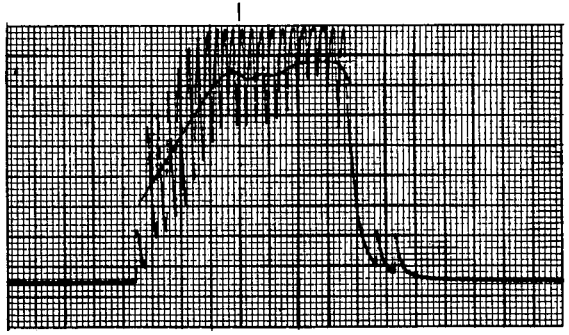
Figure 4C:
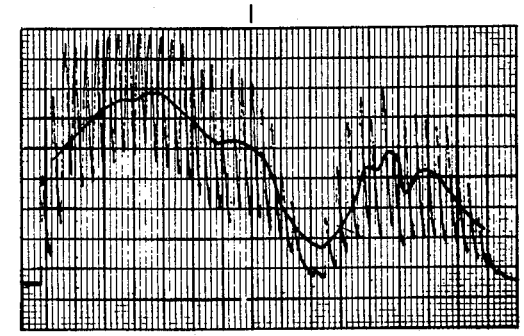

In order that the manner in which the foregoing and other objects are attained in accordance with the invention can be understood in detail, particularly advantageous embodiments thereof will be described with reference to the accompanying drawings, which form a part of this specification, and wherein:

FIGS. 1 and 2 are reproductions of records drawn in accordance with the invention and illustrating one aspect thereof;

FIGS. 3a–c are reproductions of a record drawn in a test of the method of the invention and using the apparatus of the invention;

FIGS. 4a–c are reproductions of portions of a record drawn in a test of the method of the invention and using the apparatus of the invention;

FIG. 5 is a schematic diagram, in block form, of an apparatus in accordance with the invention; and FIG. 6 is a schematic diagram of a further apparatus in accordance with the invention.

The so-called voice vibrato has been established as a semi-voluntary response which might be of value in studying deception along with certain other reactions; such as respiration volume; inspiration-expiration ratios; metabolic rate; regularity and rate of respiration; association of words and ideas; facial expressions; motor reactions; and reactions to certain narcotics; (TROVILLO, PAUL V. "A History of Lie Detection," The Journal of Criminal Law and Criminology, Mar-April May-June 1939.) however, no useable technique has been developed previously which permits a valid and reliable analysis of voice changes in the clinical determination of a subject's emotional state, opinions, or attempts to deceive.

Early experiments involving attempts to correlate voice quality changes with emotional stimuli (see SEASHORE, C. E., "Phonophotography in the Measurement of the Expression of Emotion in Music and Speech," Sci. Mo. 24:463–471 (1927); and METFESSEL, MILTON, "What is the Voice Vibrato?" Psychol. Monog. 39 (2) : 126–134 (1928) have established that human speech is affected by strong emotion. It has not yet been established that these changes are directly related to the functioning of the autonomic nervous system. In fact, the results of recent experiments by the inventors have established that detectable changes in the voice occur much more rapidly, following stress stimulation, than do the classic indications of physiological manifestations resulting from the functioning of the autonomic nervous system.

These experiments have further established two types of voice change as a result of stress. The first of these is referred to as the gross change which usually occurs only as a result of a substantially stressful situation. This change manifests itself in audible perceptible changes in speaking rate, volume, voice tremor, change in spacing between syllables, and a change in the fundamental pitch or frequency of the voice. This gross change is subject to conscious control, at least in some subjects, when the stress level is below that of a total loss of control.

The second type of voice change established was that of voice quality. This type of change is not discernible to the human ear, but is an apparently unconscious manifestation of the slight tensing of the vocal cords under even minor stress, resulting in a dampening of selected frequency variations. When graphically portrayed, the difference is readily discernible between unstressed or normal vocalization and vocalization under mild stress, attempts to deceive, or adverse attitudes. These patterns have held true over a wide range of human voices of both sexes, various ages, and under various situational conditions. This second type of change is not subject to conscious control.

As previously understood, there are two types of sound produced by the human vocal anatomy. The first type of sound is a product of the vibration of the vocal cords, which, in turn, is a product of partially closing the glottis and forcing air through the glottis by contraction of the lung cavity and the lungs. The frequencies of these vibrations can vary generally between 100 and 300 Hertz, depending upon the sex and age of the speaker and upon the intonations the speaker applies. This sound has a rapid decay time.

The second type of sound involves the formant frequencies. This constitutes sound which results from the resonance of the cavities in the head, including the throat, the mouth, the nose and the sinus cavities. This sound is created by excitation of the resonant cavities by a sound source of lower frequencies, in the case of the vocalized sound produced by the vocal cords, or by the partial restriction of the passage of air from the lungs, as in the case of unvoiced fricatives. Whichever the excitation source, the frequency of the formant is determined by the resonant frequency of the cavity involved. The formant frequencies appear generally about 800 Hertz and appear in distinct frequency bands which correspond to the resonant frequency of the individual cavities. The first, or lowest, formant is that created by the mouth and throat cavities and is notable for its frequency shift as the mouth changes its dimensions and volume in the formation of various sounds, particularly vowel sounds. The highest formant frequencies are more constant because of the more constant volume of the cavities. The formant wave forms are ringing signals, as opposed to the rapid decay signals of the vocal cords. When voiced sounds are uttered, the voice wave forms are imposed upon the formant wave forms as amplitude modulations.

It has been discovered that a third signal category exists in the human voice and that this third signal category is related to the second type of voice change discussed above. This is an infrasonic, or subsonic, frequency modulation which is present, in some degree, in both the vocal cord sounds and in the formant sounds. This signal is typically between 8 and 12 Hertz. Accordingly, it is not audible to the human ear. Because of the fact that this characteristic constitutes frequency modulation, as distinguished from amplitude modulation, it is not directly discernible on time-base/amplitude chart recordings. Because of the fact that this infrasonic signal is one of the more significant voice indicators of psychological stress, it will be dealt with in greater detail.

There are in existence several analogies which are used to provide schematic representations of the entire voice process. Both mechanical and electronic analogies are successfully employed, for example, in the design of computer voices. These analogies, however, consider the voiced sound source (vocal cords) and the walls of the cavities as hard and constant features. However, both the vocal cords and the walls of the major formant-producing cavities constitute, in reality, flexible tissue which is immediately responsive to the complex array of muscles which provide control of the tissue. Those muscles which control the vocal cords through the mechanical linkage of bone and cartilage allow both the purposeful and automatic production of voice sound and variation of voice pitch by an individual. Similarly, those muscles which control the tongue, lips and throat allow both the purposeful and the automatic control of the first formant frequencies. Other formants can be affected similarly to a more limited degree.

It is worthy of note that, during normal speech, these muscles are performing at a small percentage of their total work capability. For this reason, in spite of their being employed to change the position of the vocal cords and the positions of the lips, tongue, and inner throat walls, the muscles remain in a relatively relaxed state. It has been determined that during this relatively relaxed state a natural muscular undulation occurs typically at the 8–12 Hertz frequency previously mentioned. This undulation causes a slight variation in the tension of the vocal cords and causes shifts in the basic pitch frequency of the voice. Also, the undulation varies slightly the volume of the resonant cavity (particularly that associated with the first formant) and the elasticity of the cavity walls to cause shifts in the formant frequencies. These shifts about a central frequency constitute a frequency modulation of the central or carrier frequency.

It is important to note that neither of the shifts in the basic pitch frequency of the voice or in the formant frequencies is detectable directly by a listener, partly because the shifts are very small and partly because they exist primarily in the inaudible frequency range previously mentioned.

In order to observe this frequency modulation any one of several existing techniques for the demodulation of frequency modulation can be employed, bearing in mind, of course, that the modulation frequency is the nominal 8–12 Hertz and the carrier is one of the bands within the voice spectrum.

An example of the infrasonic variations discussed above can be observed in FIG. 1 which shows a recording made from the electrical signal resulting from a transduced voice of a normal unstressed subject. The figure depicts the pulses of the amplitude modulation of formants by a voiced signal of approximately 190 Hertz, the variations which appear as amplitude variations in FIG. 1 being amplitude representations of frequency modulation, the conversion being made by simple slope detection.

In order to more fully understand the representation of FIG. 1, the concept of a "center of mass" of this wave form must be understood. It is possible to approximately determine the midpoint between the two extremes of any single excursion of the recording pen as the wave form of FIG. 1 was drawn. If the midpoints between extremes of all excursions are marked and if those midpoints are then approximately joined by a continuous curve, it will be seen that a line approximating an average or "center of mass" of the entire wave form will result. For example, the midpoint of the excursion between the peaks identified as 10 and 11 in FIG. 1 is marked at 12. Joining all such marks, with some smoothing, results in the smooth curved line 13 in FIG. 1. The line 13 represents the infrasonic frequency modulation resulting from the undulations previously described.

As mentioned above, it has been determined that the array of muscles associated with the vocal cords and cavity walls is subject to mild muscular tension when slight to moderate psychological stress is created in the individual examination. This tension, indiscernible to the subject and similarly indiscernible by normal unaided observation techniques to the examiner, is sufficient to decrease or virtually eliminate the muscular undulations present in the unstressed subject, thereby removing the basis for the carrier frequency variations which produce the infrasonic frequency modulations.

FIG. 2 depicts an utterance similar to that of FIG. 1 but at a time of induced psychological stress. In this case, the center of mass wave form can be seen to be essentially devoid of the infrasonic variations observed in the unstressed utterance in FIG. 1, even though all other test factors and the demodulation procedures were held constant. For convenience, the center of mass is approximately indicated in FIG. 2 by line 14.

While the use of the infrasonic wave form is unique to the technique of employing voice as the physiological medium for psychological stress evaluation, the voice does provide for additional instrumented indications of aurally indiscernible physiological changes as a result of psychological stress, which physiological changes are similarly detectable by techniques and devices in current use. Of the four most often used physiological changes previously mentioned (brain wave patterns, heart activity, skin conductivity and breathing activity) two of these, breathing activity and heart activity, directly and indirectly affect the amplitude and the detail of an oral utterance wave form and provide the basis for a more gross evaluation of psychological stress, particularly when the testing involves sequential vocal responses.

FIG. 3 is a recording made during a test in which a psychological stress was induced in a female subject by having her utter a hypothetical lie in a Peak-of-Tension test. In the test the subject was asked to select one letter from a specified series of twelve letters, and to remember, but maintain in confidence, which letter she had selected. She was then asked if she had selected each of the letters in sequence. Further, she was told to respond, "I did not choose that letter" for each of the letters asked despite the fact that she had selected one. FIGS. 3a, 3b and 3c, which are a continuation of the same chart showing recordings of the oral responses by the subject when asked about each of the letters, displays an aggregate of pneumographic, cardiographic and, to a lesser degree, infrasonic influence. The signal for this display has been rather highly integrated to show more clearly the gross aggregate effect. The technique demonstrated by this chart is particularly useful in determining stress zones in tests wherein the answers constitute longer statements, wherein the statements include different words, or wherein the tests are very long requiring large numbers of statements. The evaluation is made simpler in these longer statement runs because wave form complexity is significantly reduced as compared with the wave forms shown in FIGS. 1 and 2.

The charts showing the responses on the twelve letter series from K to V show the following significant features which are indicative of physiological changes caused by the attempted deception. A marked constriction in the response to the letter K reflects the beginning-of-test tension which is normal in most overt testing situations. Generally, this initial tension would dissipate at L unless the set (the psychological predisposition) of the individual were such that the initial tension is reinforced by the tension of anticipating the approaching lie. Such is the case in this test, and tension is seen to continue at M, N and O, O being the point of deception. In addition to the observable effects of the infrasonic signal (which is normally present in relaxed speech but attenuated or absent in stressed statements) there are specific more usual physiological indicators also present which portray the changing emotional pattern of the individual. These are suppression/hyperventilation, diction stress, and significant delays in response time. The pneumographic influence gives the greatest indication of relief after the point of deception in that a noticeable increase of amplitude is indicated at the point where the individual passed the point of deception and began to compensate for the decrease in oxygen/carbon dioxide exchange occurring at K through O.

Beginning at P, the relief which is experienced by the subject is evident through the remainder of the chart with the partial exception of Q, which can be expected as a momentary fear on the part of the subject that relief at P may have been audibly evident to the examiner.

Additionally, there are certain diction stresses which may be evident as a progressive change in an individual pattern. This may or may not be audible as the subject exercises abnormal control over his diction in an attempt to maintain a static speech pattern. These indications include minor changes in individual syllable stress and changes in the concatenation patterns in the separate responses. These indicators are largely responsible for the wave form pattern (as distinguished from amplitude) of the individual response displays: they follow a slightly different progression to O, the point of deception, in that they are not as much involved with the beginning-of-test stress demonstrated by the lower amplitude at K, but cause an increasingly less complex display up to N and O, and suddenly return to their complexity with the marked psychological relief at P. With the exception of Q (for the reason previously discussed) this non-stressed pattern continues throughout the remainder of the test.

It should be noted that the opposite configuration may occur; that is, the stress may be indicated by high amplitude and a multi-form trace while relief may be shown by a drop in amplitude and more simple pattern.

This, of course, depends upon whether a given individual responds to a given psychological stimulus with excitation or depression. While the general indicators of stress and relief may differ from test to test, they are relatively stable within any individual test and, of course, the infrasonic indicator remains constant from test to test and from individual to individual.

FIGS. 4a, 4b and 4c show recordings of portions of the responses in the test discussed with reference to FIGS. 3 a–c. FIG. 4a shows the individual characteristics of the words "not" and "letter" in the response to the letter N; FIG. 4b shows recordings of the same two words for the letter O; and FIG. 4c shows these same words for the letter P. The recordings in FIGS. 4 a–c were made at a somewhat higher chart speed than were the diagrams of FIGS. 3 a–c so that each horizontal division represents a much smaller increment of time than in FIGS. 3 a–c. Additionally, the electrical signals driving the recording mechanism are integrated or filtered to a substantially lesser degree in FIGS. 4 a–c than in FIGS. 3 a–c. Thus, it is possible in FIGS. 4 a–c to observe characteristics in the individual words and, in particular, the vowel sounds in each word. The diagrams are thus "expanded" and exhibit more clearly the infrasonic characteristics of the speech which were discussed previously. In FIG. 4a, the words show relatively little of the infrasonic undulation of the type shown in FIG. 1. Similarly, in FIG. 4b (the lie) practically no infrasonic undulation appears. However, in FIG. 4c the undulation again reappears, illustrating the relief from the stress approached at the point of the lie, illustrating again the phenomenon of muscular relaxation which permits the acyclic undulations to recur. Thus, as has been indicated in the previous examples, the infrasonic wave form is obvious in the unstressed utterance and is greatly attenuated in the stressed utterance.

Some general comments about the foregoing graphical representation should be made. While the above descriptions deal with psycho-physiological relationships from some of the more significant points of view, those who are knowledgable in these areas will readily recognize the functions of the endocrine glands and sympathetic and parasympathetic nervous systems in completing the interrelationships between the psychological stimulus and the several physiological responses involved in the present invention. Similarly, while the details of the physiology of the larynx and the resonant cavities of the throat and head have been described only to the point deemed necessary to support the techniques described herein, those persons versed in human physiology will be aware of the well known physical features involved in these areas.

It should also be recognized that, while some training and experience is highly desirable in becoming adept at recognizing certain characteristics which appear in the graphical representations discussed above, it will be appreciated that considerably less training and experience is necessary to interpret charts of this nature than is necessary for the more traditionally used physiological response indicators which, in addition, have the other disadvantages hereinbefore discussed. With a minimum of training and experience one with reasonable intelligence can frequently absorb and put to use the principles and methods disclosed herein. Further, one who is already trained in the fields of polygraphic analysis and lie detector use employing the more traditional physiological manifestation indicators, can adapt to this present technique in an extremely short time.

As to the graphs themselves, the visual presentations and the manner in which they are produced can more fully be understood by a discussion of some apparatus which can be used to produce the charts previously discussed.

One embodiment of an apparatus is shown in FIG. 5 wherein a transducer 20 converts the sound waves of the oral utterances of the subject into electrical signals wherefrom they are connected to the input of an audio amplifier 21 which is simply for the purpose of increasng the power of electrical signals to a more stable, usable level. The output of amplifier 21 is connected to a filter 22 which is primarily for the purpose of eliminating some undesired low frequency components and noise components.

After filtering, the signal is connected to an FM discriminator 23 wherein the frequency deviations from the center frequency are converted into signals which vary in amplitude. The amplitude varying signals are then detected in a detector circuit 24 for the purpose of rectifying the signal and producing a signal which constitutes a series of half wave pulses. After detection, the signal is connected to an integrator circuit 25 wherein the signal is integrated to the desired degree. In circuit 25, the signal is either integrated to a very small extent, producing a wave form which is similar in configuration to that seen in FIGS. 1 and 2, or is integrated to a greater degree, producing a signal which more nearly resembles those in FIGS. 3 a–c. After integration, the signal is amplified in an amplifier 26 and connected to a chart recorder 27 which produces the visible record.

A somewhat simpler embodiment of an apparatus for producing visible records in accordance with the invention is shown in FIG. 6 wherein the acoustic signals are transduced by a microphone 30 into electrical signals which are magnetically recorded in a tape recording device 31. The signals can then be processed through the remaining equipment at various speeds and at any time, the play-back being connected to a conventional semiconductor diode 32 which rectifies the signals. The rectified signals are connected to the input of a conventional amplifier 33 and also to the movable contact of a selector switch indicated generally at 34. The movable contact of switch 34 can be moved to any one of a plurality of fixed contacts, each of which is connected to a capacitor. In FIG. 6 is shown a selection of four capacitors 35, 36, 37 and 38, each having one terminal connected to a fixed contact of the switch and the other terminal connected to ground. The output of amplifier 33 is connected to a chart recorder indicated generally at 39.

An apparatus substantially identical to that shown in FIG. 6 was used to produce the chart records shown in FIGS. 1–4, the differences between the appearances of various charts being determined by the difference in play-back speed used with tape recorder 31 and the degree of integration accomplished by the selection of capacitors with switch 34. The tape recorder used in this particular assembly of equipment was a Uher model 4000 four-speed tape unit having its own internal amplifier. The values of capacitors 35–38 were 0.5, 3, 10 and 50 microfarads, respectively, and the input impedance of amplifier 33 was approximately 10,000 ohms. The strip chart recorders used had sufficient inductance to provide a desirable amount of high frequency filtering and slope detection. Two recorders were used, one being a model O-601 Esterline-Angus recorder (FIGS. 3 a–c and 4 a–c) and the other being a galvanomic pen motor from a Keeler lie detector. As will be recognized, various other components could be, or could have been, used in this apparatus.

In the operation of the circuit of FIG. 6, the rectified wave form emerging through diode 32 is integrated to the desired degree, the time constant being selected so that the effect of the frequency modulated infrasonic wave appears as a slowly varying DC level which, as shown in FIG. 1, approximately follows the line identified by numeral 13. The excursions shown in that particular diagram are relatively rapid, indicating that the switch was connected to one of the lower value capacitors. For the diagrams of FIGS. 3 a–c, switch 34 would be set to connect capacitor 38 to the input of amplifier 33.

In this embodiment composite filtering is accomplished by the capacitor 35, 36, 37 or 38, the chart recorder, the chart-recorder amplifier, and, in the case of the playback speed reduction, the tape recorder. Frequency modulation discrimination is accomplished by the frequency-sensitive filtering at the input of the chart-recorder amplifier and by the electrical and mechanical inertia of the chart-recorder pen motor.

It will be recognized that the above described method and apparatus provides a relatively simple technique for evaluating psychological stress in a subject under examination and can be useful in detecting efforts at deception. It will also be recognized that the complete absence of connections to the subject under examination permits the apparatus to be used with a subject who does not know that he is being examined and also permits examination of subjects at a remote distance, such as over telephone lines or other communications networks. An example of this technique is the recording of the oral utterances of a person, or several individuals, appearing on a television program, notably one program in which each of three parties claimed to be a specific individual but only one of the parties was telling the truth. Recordings of the statements by each party, processed in accordance with the method of the present invention on an apparatus such as that shown in FIG. 6, provided recordings from which the individual telling the truth could be readily identified. Thus, the apparatus is much less limited than any previously known stress analyzing device.

While certain advantageous embodiments have been chosen to illustrate the invention it will be understood by those skilled in the art that various changes and modifications can be made therein without departing from the scope of the invention as defined in the appended claims.

What is claimed is:

1. A method of identifying physiological manifestations of psychological stress in a human subject comprising the steps of
    converting an oral utterance by the subject from sound energy into electrical signals;
    emphasizing those portions of the electrical signals which represent inaudible variations in the infrasonic frequency modulation of the voice of the subject;
    recording signals representative of the emphasized portions of the electrical signals on a visually observable medium; and
    observing the visual record of the utterance to determine increases and decreases in modulation variations, the degree of presence of the modulation constituting an inverse measure of the stress.

2. An apparatus for producing a display of characteristics of oral utterances of a subject, which display can be observed for indications of involuntary physiological manifestations of psychological stress, the apparatus comprising the combination of
    transducer means for converting the oral utterances into electrical signals,
    said transducer means including means for producing a magnetic recording of the oral utterances to permit repeated processing of said utterances to emphasize different characteristics;
    signal processing means for receiving the electrical signals and for emphasizing preselected inaudible involuntary stress indicating characteristics thereof; and
    means for displaying the emphasized characteristics.

3. An apparatus according to claim 2 wherein said signal processing means includes
    means for detecting infrasonic frequency variations in said electrical signals and for providing to said means for displaying an amplitude-varying signal representative of said variations.

4. An apparatus for producing a display of characteristics of oral utterances of a subject, which display can be observed for indications of involuntary physiological manifestations of psychological stress, the apparatus comprising the combination of
    transducer means for converting the oral utterances into electrical signals;
    signal processing means for receiving the electrical signals and for emphasizing preselected inaudible involuntary stress indicating characteristics thereof; and
    means for displaying the emphasized characteristics,
    said signal processing means including means for detecting infrasonic frequency variations in said electrical signals and for providing to said means for displaying an amplitude-varying signal representative of said variations, and means for integrating said electrical signals.

5. An apparatus for producing a display of characteristics of oral utterances of a subject, which display can be observed for indications of involuntary physiological manifestations of psychological stress, the apparatus comprising the combination of
    transducer means for converting the oral utterances into electrical signals;
    signal processing means for receiving the electrical signals and for emphasizing preselected inaudible involuntary stress indicating characteristics thereof,
    said signal processing means including means for integrating said electrical signals; and
    means for displaying the emphasized characteristics.

6. An apparatus according to claim 5 wherein said signal processing means includes means for emphasizing composite characteristics resulting from aggregate physiological changes.

7. An apparatus according to claim 5 wherein
    said signal processing means includes demodulator means for converting the inaudible infrasonic frequency modulations representative of the characteristics to be analyzed in said electrical signals to amplitude modulations; and
    said means for displaying includes means for recording the amplitude modulations on a visible record.

8. An apparatus for producing a visible indication of involuntary stress manifestations comprising the combination of
- means for converting the oral utterances of a subject into electrical signals;
- discriminator means for converting frequency deviations in said electrical signals into amplitude variations;
- detector means for rectifying said electrical signals to produce signals having unidirectional pulses;
- means for partially integrating said signals with respect to time; and
- means for accepting the integrated signals and for producing a visible indication of the degree of presence of an inaudible infrasonic component in said deviations,
- the degree of presence of said component constituting a measure of psychological stress in the subject.

9. An apparatus for producing a visible record of characteristics of oral utterances of a human subject, which characteristics are not discernible by the unaided human ear, for analysis of involuntary psychological stress manifestations, the apparatus comprising the combination of
- transducer means for converting the oral utterances into electrical signals;
- demodulator means for converting the inaudible infrasonic frequency modulations representative of the characteristics to be analyzed in said electrical signals to amplitude modulations;
- means for recording the amplitude modulations on a visible record; and
- integrator circuit means for partially integrating the electrical signal output from said demodulator means to emphasize the amplitude modulation in the signals representative of inaudible infrasonic frequency modulation components present in the voice of the subject before recording,
- the absence and degree of presence of said modulations being observable as indications of the presence and degree of presence of psychological stress.

* * * * *